United States Patent [19]

Maul et al.

[11] Patent Number: 5,124,487
[45] Date of Patent: Jun. 23, 1992

[54] CATALYTIC REDUCTION OF NITRILES TO ALDEHYDES

[75] Inventors: James J. Maul, Grand Island; Garra C. Lester, Eden; Henry C. Lin, Grand Island, all of N.Y.

[73] Assignee: Occidental Chemical Corporation, Niagara Falls, N.Y.

[21] Appl. No.: 739,956

[22] Filed: Aug. 5, 1991

[51] Int. Cl.$^5$ .................. C07C 45/00; C07C 45/44
[52] U.S. Cl. ................. 568/436; 568/426; 568/437
[58] Field of Search ............. 568/436, 426, 437

[56] References Cited

U.S. PATENT DOCUMENTS

| | | | |
|---|---|---|---|
| 2,945,862 | 7/1969 | Mignonac et al. | 568/437 |
| 4,111,998 | 9/1978 | Decor | 568/436 |
| 4,383,949 | 5/1983 | Maurer et al. | 568/436 |
| 4,500,721 | 2/1985 | Yamachika et al. | 568/436 |

FOREIGN PATENT DOCUMENTS

| | | | |
|---|---|---|---|
| 10689 | 4/1897 | United Kingdom | 568/436 |
| 811527 | 4/1959 | United Kingdom | 568/436 |

OTHER PUBLICATIONS

Backeberg et al "Jour. of the Chem. Soc." (London) Oct. 1962 pp. 3961–3963.
T. van Es & B. Staskun, Organic Syntheses, 51, 20 (1971).

*Primary Examiner*—Werren B. Lone
*Attorney, Agent, or Firm*—James F. Tao; Arthur S. Cookfair

[57] ABSTRACT p-Trifluoromethyl benzaldehydes are prepared by the catalytic reduction reaction of p-trifluoromethyl benzonitriles with hydrogen in an aqueous formic acid media in the presence of a nickel/aluminum alloy catalyst.

9 Claims, No Drawings

CATALYTIC REDUCTION OF NITRILES TO ALDEHYDES

BACKGROUND OF THE INVENTION

1. Field of the Invention

This invention relates to a process for the production of trifluoromethyl benzaldehydes, useful as chemical intermediates in the further production of pesticides.

2. Prior Art

Benzaldehydes are useful for a variety of industrial applications and various processes for the production of benzaldehydes are found in the literature.

U.S. Pat. No. 4,111,998 discloses a process for the preparation of an aromatic aldehyde by reduction of the corresponding acid chloride using hydrogen in the presence of a palladium catalyst and a tertiary amide.

U.S. Pat. No. 4,383,949 discloses a process for the preparation of a 3-bromo-4-fluorobenzaldehyde acetal by reaction of the corresponding benzoic acid halide with ammonia to form an imide, dehydrating the imide to form 3-bromo-4-fluorobenzonitrile, and reacting the nitrile with formic acid in the presence of a catalyst to form the benzaldehyde. The benzaldehyde is then converted to the benzaldehyde acetal.

U.S. Pat. No. 2,945,862 teaches a process for the preparation of aldehydes by catalytic hydrogenation of the corresponding nitriles in the presence of an aqueous phase and in the presence of a metal catalyst such as reduced nickel.

U.S. Pat. No. 4,500,721 discloses a process for the preparation of benzaldehydes from benzonitriles by catalytic reduction in the presence of an acid using a Raney nickel catalyst pretreated with a copper salt.

T. vanEs and B. Staskun, Organic Syntheses, 51, 20 (1971) describe the reduction of an aromatic nitrile to an aldehyde in the absence of hydrogen using a stoichiometric excess of nickel/aluminum alloy reagent as a reducing agent in 75% formic acid. The process is not a catalytic reduction but rather reduction where the nickel/aluminum alloy is a sacrificial reagent.

SUMMARY OF THE INVENTION

It has now been found that p-trifluoromethyl benzaldehydes may be prepared by the catalytic reduction of p-trifluoromethyl benzonitriles in an aqueous acid medium in the presence of a nickel/aluminum alloy catalyst. The process of the invention is illustrated by the following equation:

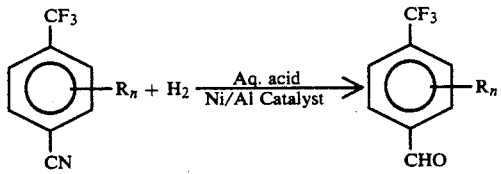

where R is $CF_3$, or $CH_3$; n is 0–4.

The advantages of the present invention over the prior art processes are as follows:

1. The nickel/aluminum catalyst employed in the present process is substantially less expensive than the Raney nickel catalyst employed in the prior art processes.

2. The present catalyst is more convenient to use and considerably safer than Raney nickel. The latter must be stored under inert gas or under water since it will ignite spontaneously in air. It is considered a dangerous fire risk.

3. In the present process the nickel/aluminum alloy is employed in catalytic quantities rather than reagent quantities, thus minimizing cost as well as metal waste disposal problems.

DETAILED DESCRIPTION OF THE INVENTION

In accordance with this invention, the catalytic reduction of p-trifluoromethyl benzonitriles to the corresponding p-trifluoromethyl benzaldehydes is carried out in a aqueous acidic medium. Suitable aqueous acids include, for example, sulfuric acid, acetic acid, formic acid and the like. The preferred reaction medium is aqueous formic acid, most preferably 10–30% aqueous formic acid.

The catalyst employed is a 50/50 wt % nickel/aluminum alloy, preferably in powder form. The amount of catalyst may vary but is preferably in the range of about 3.0–22 weight percent, based on the weight of organic substrate and about 0.5 to 1.5 weight percent, based on the volume of aqueous acid.

The amount of organic substrate, i.e., trifluoromethyl benzonitrile, may vary considerably but will preferably be in the range of about 7 to 15% by weight of the substrate, based on the volume of aqueous acid.

Based on the foregoing considerations, a preferred reaction mixture would contain about 0.5 to 1.5 g of powdered 50/50 nickel/aluminum alloy and about 7.0 to 15.0 g of p-trifluoromethyl benzonitrile per 100 mL of 15–25% aqueous formic acid. The reaction is conveniently carried out in closed vessel with hydrogen being supplied to the reaction mixture at a pressure of 1 atmosphere or greater. The temperature is typically maintained at about 50° to 100° Celsius, preferably about 70°–90° Celsius. It is important that the reaction mixture be agitated, e.g. by shaking, stirring, etc. to assure continuous mixing of the four phases, aqueous acid, organic substrate, catalyst, and hydrogen gas.

The following examples are provided to further illustrate the present invention and the manner in which it may be practiced.

EXAMPLE 1

A Parr hydrogenation bottle was purges with $N_2$ and then charged with 25 g of 4-trifluoromethyl benzonitrile, 250 mL of 75% aqueous formic acid and 3.0 g of powdered nickel/aluminum alloy catalyst (50/50). The reaction mixture was shaken at 80° C. with $H_2$ gas (3 atmospheres pressure) for 16 hours. The reaction mixture was continuously extracted with $CH_2Cl_2$ and analyzed via Internal Standard GLC which indicated 87.9% yield of 4-trifluoromethyl benzaldehyde.

EXAMPLE 2

A three necked flask was purged with $N_2$ and then charged with 125 g of p-trifluoromethyl benzonitrile (PTFMBN), 1250 mL of 15% aqueous formic acid and 22.5 g of nickel/aluminum alloy. The reaction mixture was stirred at 80 ° C. under an $H_2$ gas (1 atmosphere) for 10 hours. The reaction mixture was extracted with $CH_2Cl_2$ and filtered. The liquid was distilled to yield 94.5 g (75% yield) (bp 70° C. / 12 Torr.) of p-trifluoromethyl benzaldehyde (PTFMBAL).

EXAMPLE 3

A Parr hydrogenation bottle was purged with $N_2$ and then charged with 5 g of 4-trifluoromethyl benzonitrile, 50 mL of 35% aqueous acetic acid and 0.6 g of nickel-/aluminum alloy. The reaction mixture was shaken at 80° C. with $H_2$ gas (3 atmospheres pressure) for 16 hours, then allowed to settle, forming an aqueous phase and an organic phase. Analysis of the organic phase by Internal Standard GLC indicated, in GC area percent, 40% p-trifluoromethyl benzaldehyde.

EXAMPLE 4

A Parr hydrogenation bottle was purged with $N_2$ and then charged with 5 g of 4-trifluoromethyl nitrile, an aqueous solution of $H_2SO_4$ (4.2 g conc. $H_2SO_4$ in 51 g of $H_2O$) and 0.6 g of nickel/aluminum alloy (50/50). The reaction was shaken at 45° C. with $H_2$ gas (3 atmospheres pressure) for 23 hours. The reaction mixture was extracted with $CH_2Cl_2$ and the extract was filtered through celite. Analysis via GLC indicated, in area percent, 60% p-trifluoromethyl benzaldehyde.

What is claimed is:

1. A process for the preparation of p-trifluoromethyl benzaldehydes of the formula

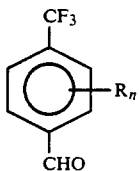

where R is $CF_3$ or $CH_3$ and n is 0 - 4 which comprises reacting a p-trifluoromethyl benzonitrile of the formula

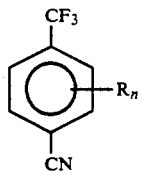

where R and n are as set forth above, with hydrogen in an aqueous acid medium in the presence of a nickel-/aluminum alloy catalyst.

2. A process according to claim 1 wherein n is 0.

3. A process according to claim 2 wherein the aqueous acid medium is aqueous formic acid.

4. A process according to claim 3 wherein the aqueous acid medium is 10–30% aqueous formic acid.

5. A process according to claim 2, carried out at a temperature of about 50° to 100 ° C.

6. A process according to claim 4, carried out at a temperature of about 50° to 100° Celsius, with agitation, at a pressure of about 1 atmosphere or higher.

7. A process according to claim 5 wherein the nickel-/aluminum alloy catalyst is present in an amount of about 3.0 to 22% by weight, based on the weight of p-trifluoromethyl benzonitrile.

8. A process for the preparation of p-trifluoromethyl benzaldehyde which comprises reacting p-trifluoromethyl benzonitrile with hydrogen in 10–30% aqueous formic acid in the presence of about 3.0 to 22.0 weight percent of powdered nickel/aluminum alloy, based on the weight of p-trifluoromethyl benzonitrile, at a temperature of about 50° to 100° Celsius at atmospheric or superatmospheric pressure.

9. A process according to claim 8 carried out at a temperature of about 70° to 90° Celsius.

* * * * *